US005970112A

United States Patent [19]

Hsieh

[11] Patent Number: 5,970,112

[45] Date of Patent: Oct. 19, 1999

[54] SMART COLLIMATION BASED ON A SINGLE SCOUT SCAN IN A COMPUTED TOMOGRAPHY SYSTEM

[75] Inventor: Jiang Hsieh, Brookfield, Wis.

[73] Assignee: General Electric Company, Milwaukee, Wis.

[21] Appl. No.: 09/047,826

[22] Filed: Mar. 25, 1998

[51] Int. Cl.[6] .......... A61B 6/03

[52] U.S. Cl. .......... 378/8; 378/901

[58] Field of Search .......... 378/4, 8, 901

[56] References Cited

U.S. PATENT DOCUMENTS

| | | | |
|---|---|---|---|
| 5,727,041 | 3/1998 | Hsieh | 378/4 |
| 5,812,628 | 9/1998 | Hsieh | 378/8 |

*Primary Examiner*—David Vernon Bruce

*Attorney, Agent, or Firm*—John S. Beulick; Christian G. Cabou; Phyllis Y. Price

[57] ABSTRACT

A CT system having an adjustable pre-patient collimator and a partial volume artifact reduction algorithm is described. In one embodiment, a scout scan is performed to collect scout scan data. Utilizing the scout scan data, the algorithm identified the boundaries and radius of a partial volume artifact producing object. The algorithm then determines an average attenuation coefficient and an attenuation index of the object. The object radius, the attenuation coefficient and attenuation index are then graded to identify the object. A collimator aperture index is then determined based upon a variation of the attenuation characteristic along the z axis for the identified object. Utilizing the collimator aperture index, the CT system computer adjusts the collimator aperture for the appropriate size to eliminate, or significantly reduce, partial volume artifacts.

22 Claims, 3 Drawing Sheets

SMART COLLIMATION BASED ON A SINGLE SCOUT SCAN IN A COMPUTED TOMOGRAPHY SYSTEM

FIELD OF THE INVENTION

This invention relates generally to computed tomography (CT) imaging and more particularly, to reducing partial volume image artifacts in an image reconstructed from scan data.

BACKGROUND OF THE INVENTION

In at least some known CT system configurations, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector.

In an axial scan, the projection data is processed to construct an image that corresponds to a two dimensional slice taken through the object. One method for reconstructing an image from a set of projection data is referred to in the art as the filtered backprojection technique. This process converts the attenuation measurements from a scan into integers called "CT numbers" or "Hounsfield units", which are used to control the brightness of a corresponding pixel on a cathode ray tube display.

During scanning, the x-ray beam is known to spread along a z-axis to form a "scan plane". For each image slice, the object to be imaged often only partially intrudes on the scan plane. Specifically, the object is only partially subjected to the x-ray beam, thus causing inconsistencies in the projection data. When reconstructing an image for a particular slice, these inconsistencies generate incorrect CT numbers, streaks, and other artifacts in generated images. As the slice thickness is increased, the likelihood of partial intrusion increases. The image errors created by partial intrusion are often referred to as "partial volume artifacts".

To reduce partial volume artifacts, known CT systems rely upon human operators to either identify the partial volume artifacts, or to take preventative measures to avoid the generation of such artifacts. The preventative measures include scanning an area of the object, stopping the scan, altering x-ray source collimators, and continuing the scan. For example, a 10 mm collimator which provides a slice thickness of 10 mm, may be used when scanning a region with few bony structures. However, when scanning a region with multiple bony structures, a 3 mm collimator which provides a slice thickness of 3 mm, may be used. This method is both time consuming and cumbersome. Furthermore, this method is neither practical nor efficient when scanning adjacent differing regions. The operator must, based on past experience, select slices of sufficiently small thickness to ensure constant attenuation characteristics across the slice, i.e., to ensure that the object does not partially intrude on the scan plane. However, thin slices typically require significantly long scanning times and x-ray tube cooling delays. Conversely, thicker slices are preferred for improving x-ray photon flux. As a result, the operator is forced to weigh these alternatives and make the proper choice.

Therefore, it is desirable to eliminate operator involvement in the determination of the optimal slice thickness. It is also desirable to eliminate, or substantially reduce, partial volume artifacts without significantly reducing CT system efficiency.

SUMMARY OF THE INVENTION

These and other objects may be attained by a CT system having a partial volume artifact reduction algorithm which, in one embodiment, determines the proper aperture size of a pre-patient collimator. Particularly, prior to performing a CT scan on a patient, a scout scan is performed. After the scout scan data is pre-processed, the algorithm identifies objects or regions that can cause a partial volume artifact and determines the appropriate aperture size for each area of the patient to substantially reduce or eliminate partial volume artifacts in the CT scan.

More specifically, in accordance with one embodiment of the present invention, the adjustable collimator aperture is set to 1 mm. The scout scan is then completed and the scout scan data is pre-processed. The algorithm then utilizes the scout data to identify the boundaries of the object of interest and estimate the radius of the object. In order to declare the object, for example, to be a human head, a set of criteria must be met. The algorithm utilizes an average attenuation coefficient, an attenuation index of the object, and the radius of the object to identify the object. A membership grade is assigned for each criteria to improve the quality of identification. Specifically, a final membership grade is determined utilizing an object radius membership grade, an average attenuation membership grade and an attenuation membership grade. The final membership grade is then evaluated to define the object.

A variation of the attenuation characteristic is then determined along the z axis for the object by calculating the difference between the measured projection and an average projection for a specific slice thickness. In one embodiment, the variation of the attenuation characteristic calculates the differential signal between the scout scan 1 mm slice thickness and the signal if the collimator were changed to a different thickness, for example 10 mm. A weighting function is then applied to the attenuation characteristic to compensate for the location of most partial volume streaks within the object. A collimator aperture index, which represents the desired slice thickness to maintain a constant variation in the z axis, is then determined.

Utilizing the collimator aperture index, the computer automatically adjusts the size of the collimator aperture for each area to be scanned. As a result, each area to be scanned may have a distinct slice thickness to significantly reduce, or eliminate, partial volume artifacts.

The above described system eliminates operator involvement in the determination of the optimal slice thickness. In addition, partial volume artifacts are eliminated, or significantly reduced, without significantly reducing CT system efficiency.

DETAILED DESCRIPTION

Figure 1:
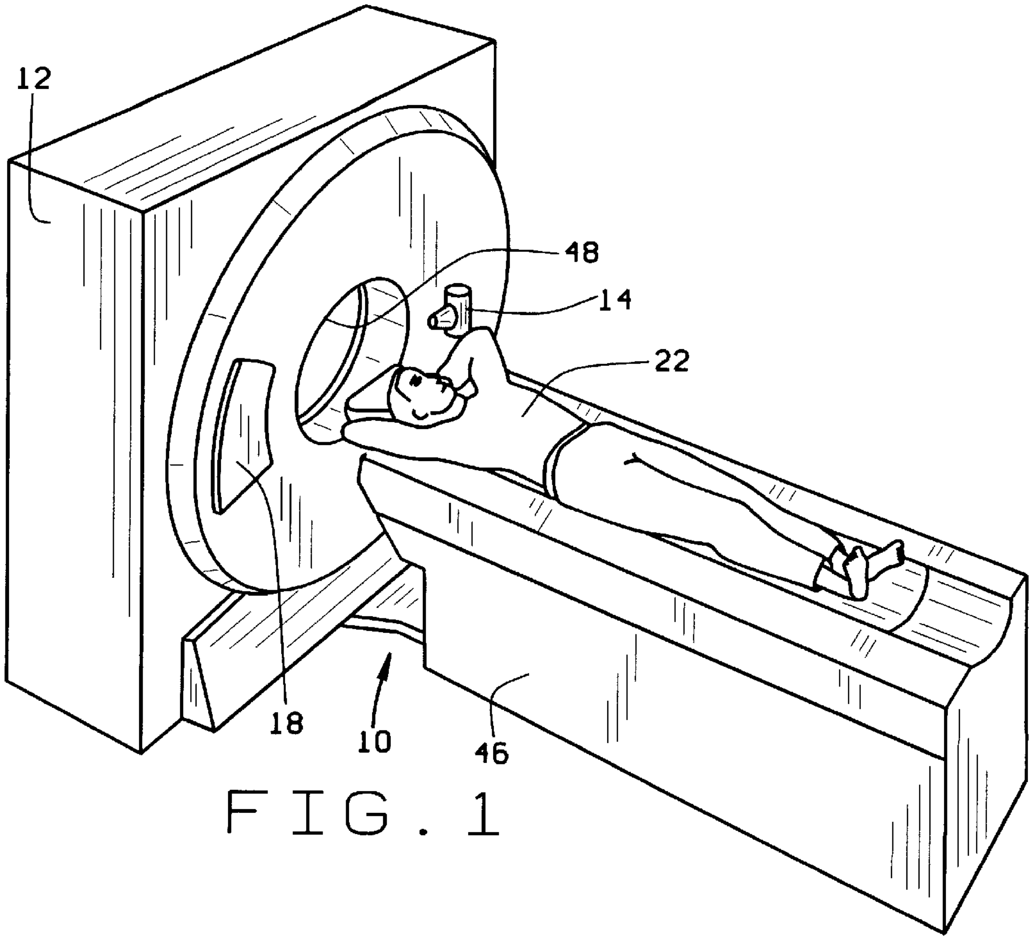
FIG. 1 is a pictorial view of a CT imaging system.
Figure 2:
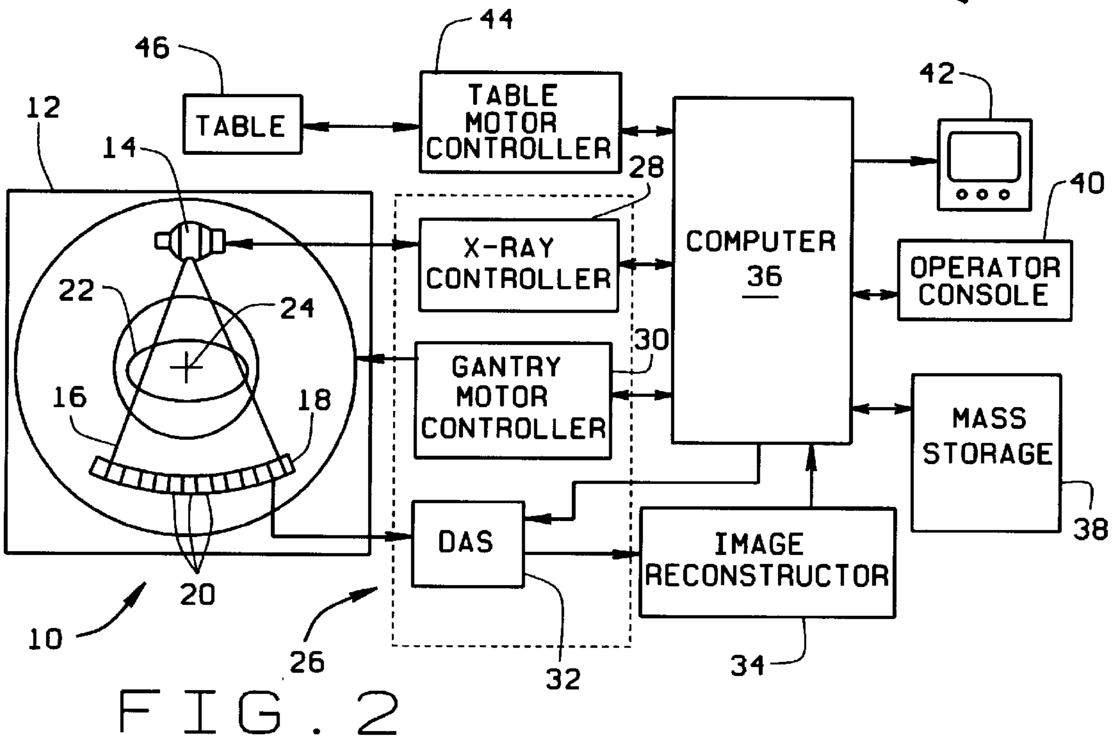
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. X-ray beam 16 is collimated by a collimator (not shown in FIGS. 1 or 2) to lie within an X-Y plane of a Cartesian coordinate system and generally referred to as an "imaging plane". Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
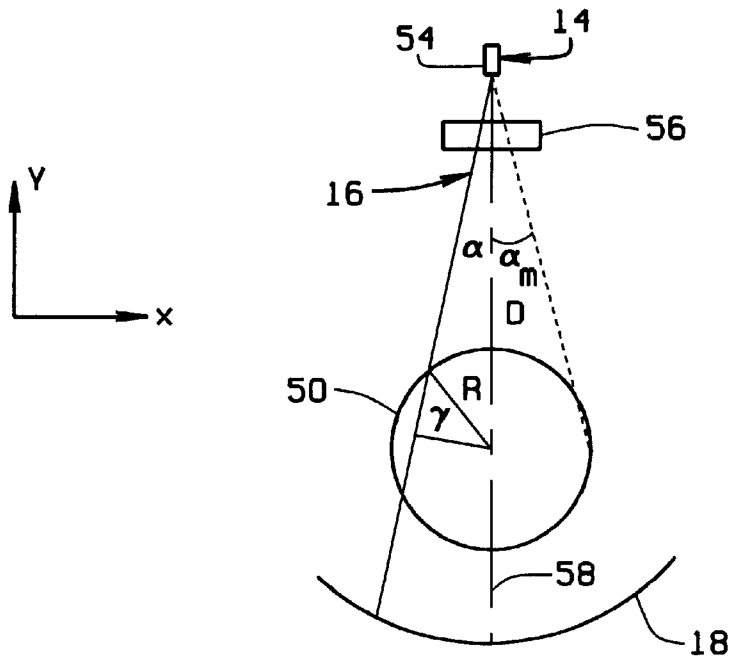
FIG. 3 is a schematic illustration of an x-ray source, a detector, and a partially intruded object of interest in a x-y plane.

FIG. 3 is a schematic illustration of x-ray source 14, detector array 18, and an object of interest 50, in the x-y plane. X-ray source 14 projects x-ray beam 16 toward object of interest 50 and detector array 18. Object of interest 50 typically is a portion of patient 22 being scanned. More particularly, x-ray beam 16 emanates from a focal spot 54 of x-ray source 14. X-ray beam 16 is collimated by a variable, or adjustable, collimator 56, and collimated beam 16 is projected toward detector array 18. Beam 16 has a fan beam axis 58 centered within fan beam 16.

Figure 4:
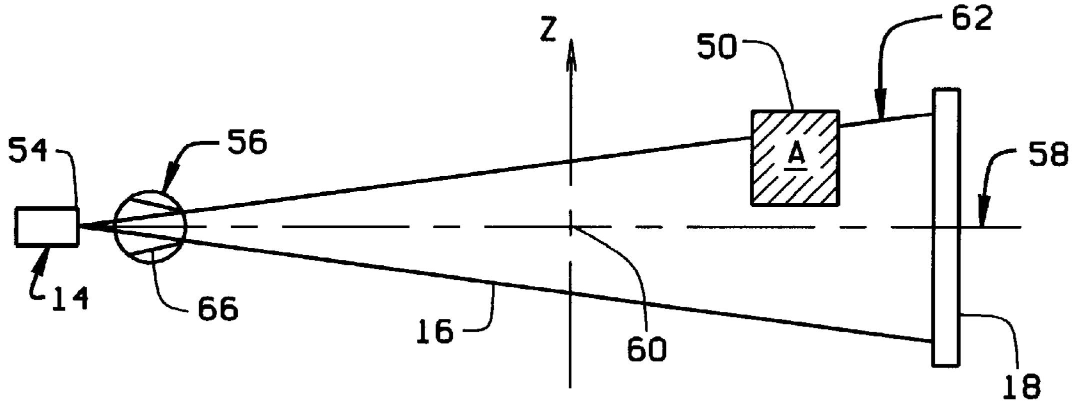
FIG. 4 is a schematic illustration of the x-ray source, the detector, and a partially intruded object of interest in a z-axis direction.

FIG. 4 is a schematic illustration of source 14, array 18, and object of interest 50, in a z-axis direction. X-ray beam 16 has an iso-center 60, and defines a "scan plane" 62. The width of x-ray beam 16 at iso-center 60 is referred to herein as "slice thickness". As shown in FIG. 4, x-ray beam 16 only passes through a portion of object of interest 50, i.e., object of interest 50 "partially intrudes" on scan plane 62. As explained above, this partial intrusion causes errors and artifacts in slice images of object of interest 50.

Collimator 56 has a substantially circular cross-sectional shape and an aperture 66 extends through variable collimator 56. A plurality of other collimator apertures (not shown) also are formed in and extend through variable collimator 56, and each aperture corresponds to a particular slice thickness, or slice width. For example, aperture 66 may correspond to a 10 mm slice width and another aperture may correspond to a 5 mm slice width. If a scan is to be performed for a 10 mm slice, then aperture 66 is aligned with expected x-ray focal spot 54 and restricts beam 16 projected from focal spot 54 to 10 mm. Similarly, if a scan is to be performed for a 5 mm slice, then a 5 mm slice thickness aperture 66 is aligned with expected x-ray focal spot 54 to restrict beam 16 to 5 mm. Variable collimator 56 is well known in the art.

The partial volume artifact reduction algorithm described below may be implemented in computer 36 and practiced using data collected by DAS 32. It will be apparent to those skilled in the art, of course, that such algorithm could be practiced in other components. For example, the algorithm may be practiced directly in image reconstructor 34 so that corrected data is supplied to computer 36.

In accordance with one embodiment of the present invention, after patient 22 is positioned on table 46, collimator aperture 66 is adjusted by computer 36 for a slice thickness of 1 mm. A CT scout scan is then performed to gather scout scan data, in a manner known in the art. The resulting scout data, after being processed, i.e, offset correction, primary speed correction, double channel expansion, normalization, aircal, minus logarithm, and beam hardening correction, represents the measured line integral of the attenuation coefficients of the object viewed at the scout angle (typically at 0, 90, 180, or 270 degrees). Adjusting collimator aperture 66 to 1 mm ensures no significant partial volume artifacts will be present in the scout scan data.

The boundary of the object of interest (OOI), for example, the head of patient 22, is then determined. Although the patient's head will be discussed in the following example, the algorithm may be used to identify other portions of a patient's body as well.

In determining the boundaries of the OOI, first the centroid of each projection, $c(\gamma)$, is determined. The object boundaries, $b_1(\gamma)$ and $b_r(\gamma)$, are then defined as the location where the projection intensity reaches a certain fraction, $\delta$, of the projection intensity at the centroid $c(\gamma)$. Since multiple locations may be found that satisfy this condition, the nearest location to centroid $c(\gamma)$ on each side is selected as the boundary to avoid the situation where foreign objects may be mistakenly considered as part of the human head. In most cases, for example, $\delta=0.4$.

To further reduce the possibility of foreign object inclusion, centroid, $c(\gamma)$, and boundaries, $b_1(\gamma)$ and $b_r(\gamma)$, are further filtered in the z axis. In one embodiment, a median filter is applied first, followed by a box car filter. Other types of filters may also be used.

The radius of the object is then determined, assuming the object, for example the head of patient 22, is uniform and of round shape. The relationship between the boundary distance and the radius of the object is determined as follows:

$$R = \frac{D\sin(\alpha)}{\sqrt{1-\delta^2}} \tag{1}$$

where:

R=radius of the object,

α=angle formed by the "boundary rays" and the iso-ray,

δ=parameter to determine the object boundary, and

D=distance between the x-ray source and the iso-center.

An average attenuation coefficient, $\mu$, of the measured object is then determined by:

$$\mu = \frac{\int_{-\gamma_m}^{\gamma_m} p(\gamma)d\gamma}{2\int_0^{\alpha_m}\sqrt{R^2-([D\sin(\gamma)])^2}\,d\gamma} \tag{2}$$

where p(γ) is the measured projection at detector angle γ.

To further enhance the partial volume artifact reduction algorithm, an attenuation index of the object, ξ, is defined as:

$$\xi = R^{-1}\int_{-\gamma_m}^{\gamma_m} p(\gamma)d\gamma \tag{3}$$

In order to declare an object to be a human head, a set of criteria must be met. First, the radius of the object, R, has to fall within the pre-defined range. Second, the average attenuation of the object, $\mu$, has to fall within a specified range. Third, the attenuation index of the object, ξ, must be within pre-defined limits. However to minimize errors, a membership grade is assigned for each testing criterion. An object radius membership grade, $R_g$, is:

$$R_g = 3R_g'^2 - 2R_g'^3 \tag{4}$$

where:

$$R_g' = \begin{cases} 0 & \text{if } R \le R_{\min} \\ \frac{R-R_{\min}}{R_{\max}-R_{\min}} & \text{if } R_{\min} < R \le R_{\max} \\ 1 & \text{if } R > R_{\max} \end{cases}$$

where:

$R_{\min} = 50$ mm and $R_{\max} = 70$ mm.

An average attenuation membership grade, $\mu_g$, is determined as follows:

$$\mu_g = 3\mu_g'^2 - 2\mu_g'^3 \tag{5}$$

where:

-continued $$\mu_g' = \begin{cases} 0 & \text{if } \mu \le \mu_1 \\ \frac{\mu-\mu_1}{\mu_2-\mu_1} & \text{if } \mu_1 < \mu \le \mu_2 \\ 1 & \text{if } \mu_2 < \mu \le \mu_3 \\ \frac{\mu_4-\mu}{\mu_4-\mu_3} & \text{if } \mu_3 < \mu \le \mu_4 \\ 0 & \text{if } \mu > \mu_4 \end{cases}$$

where $\mu_1 = 0.008$, $\mu_2 = 0.010$, $\mu_3 = 0.025$ and $\mu_4 = 0.030$.

An attenuation index membership grade, $\xi_g$, is:

$$\xi_g = 3\xi_g'^2 - 2\xi_g'^3 \tag{6}$$

where:

$$\xi_g' = \begin{cases} 1 & \text{if } \xi \le \xi_{\min} \\ \frac{\xi_{\max}-\xi}{\xi_{\max}-\xi_{\min}} & \text{if } \xi_{\min} < \xi \le \xi_{\max} \\ 0 & \text{if } \xi > \xi_{\max} \end{cases}$$

where:

$\xi_{\min} = 13$ and $\xi_{\max} = 15$.

A final membership grade, H, is defined as:

$$H = R_g \mu_g \xi_g \tag{7}$$

where the object is considered a human head if H>0.5.

Next, a variation of the attenuation characteristic, Δ(γ), is measured along the z axis for the object as follows:

$$\Delta(\gamma) = p(\gamma) - \bar{p}(\gamma) \tag{8}$$

where:

Δ(γ) is the measured projection, and $\bar{p}(\gamma)$ is the average projection along the z axis -x mm region.

In one embodiment, for example, x=10 so that Δ(γ) is determined using the differential signal between the measured 1 mm slice thickness and the signal if the collimator were changed to 10 mm. In an alternative embodiment, $\bar{p}(\gamma)$ may be a weighted average that simulates the x-ray distribution in the Z-axis direction.

Figure 5:
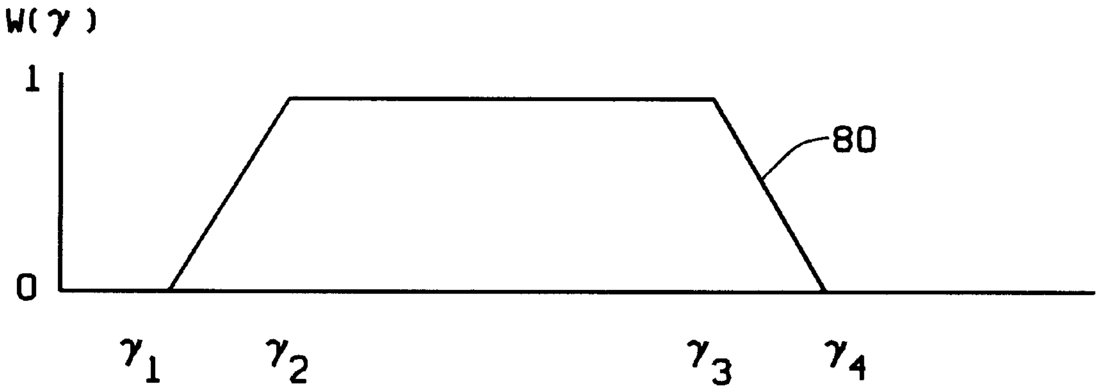
FIG. 5 is a weighting function in accordance with one embodiment of the present invention.

As most partial volume streaks occur near the center of the head, differential signal Δ(γ) is adjusted by a weighting function 80 as shown in FIG. 5. $\gamma_1$, $\gamma_2$, $\gamma_3$, $\gamma_4$ are determined by:

$$\begin{aligned} \gamma_1 &= (1-\eta_b)c(\gamma) + \eta_b b_l(\gamma) \\ \gamma_2 &= (1-\eta_c)c(\gamma) + \eta_c b_l(\gamma) \\ \gamma_3 &= (1-\eta_c)c(\gamma) + \eta_c b_r(\gamma) \\ \gamma_4 &= (1-\eta_b)c(\gamma) + \eta_b b_r(\gamma) \end{aligned} \tag{9}$$

where:

$\eta_c$=0.85, $\eta_b$=0.95, c(γ) is the centroid of the object, and $b_1(\gamma)$ and $b_r(\gamma)$ are the left and right boundaries.

A collimator aperture index, $A_{index}$, which represents the desired slice thickness to maintain a constant variation in z is then determined. Collimator aperture index, $A_{index}$, is inversely proportional to the total weighted differential signal as follows:

$$A_{index} = \frac{\theta}{\int_{-\gamma_m}^{\gamma_m} \Delta(\gamma) w(\gamma) d\gamma} \quad (10)$$

where θ is, in one embodiment, 60. Equation (10) represents a gantry tilt angle of zero so that CT scan plane 54 is perpendicular to the z axis. If a CT scan needs to be performed with non-zero degree tilt, $A_{index}$ will occur along the gantry tilting angle.

Utilizing $A_{index}$, computer 36 adjusts collimator aperture 66. Computer 36, for example, adjusts aperture 66 to an appropriate aperture size based on aperture index, $A_{index}$ for each area to be scanned. For example, aperture 66 may be set to 3 mm when $3 \leqq A_{index} < 5$. Additionally, a minimum aperture size may be determined so that, for example, the smallest aperture used in the scan should not be less than 3 mm, then the decision criterion for a 3 mm aperture becomes: $A_{index} < 5$.

The information obtained from the scout image may also be used to guide the correction of the partial volume artifact in the image reconstruction process. This is useful when the dynamic change of the collimator aperture is not desired. For example, in an emergency situation, an operator would want to minimize the scan time by using a large aperture. The collimator aperture index, $A_{index}$, could then be used to correct for the partial volume artifact in image reconstructor 34.

Additional constraints may be added to the algorithm to guard against frequent collimator aperture changes and to improve patient throughput. For example, when the number of slices using a certain collimator thickness is less than a predefined threshold, collimator aperture 66 may be selected as the smallest aperture among the nearby groups. Additionally, the number of different aperture openings 66 may be small or large depending on the requirements of system 10.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the partial volume artifact reduction algorithm is not limited to practice in connection with only axial scans. The algorithm may be used with other types of scans, such as helical scans. Accordingly, the spirit and scope of the invention are to be limited only by the terms of the appended claims.

I claim:

1. A method for reducing partial volume artifacts in scan data of a patient, the scan data collected in a computed tomography system having an adjustable slice thickness collimator, said method comprising the steps of:

performing a scout scan of the patient;

processing the obtained scout scan data to detect the presence of a partial volume artifact producing object; and adjusting the collimator slice thickness based on the presence of the detected object.

2. A method in accordance with claim 1 wherein processing the scout scan data comprises the steps of:

identifying the boundaries of the object;

estimating the radius of the object;

determining an average attenuation coefficient; and determining an attenuation index.

3. A method in accordance with claim 2 further comprising the step of:

identifying anatomical characteristics of the object using at least one of the estimated radius of the object, the average attenuation coefficient, and the attenuation index.

4. A method in accordance with claim 2 wherein estimating the radius of the object is:

$$R = \frac{D\sin(\alpha)}{\sqrt{1-\delta^2}}$$

where:

R=radius of the object;

α=angle formed by the boundary rays and the iso-ray;

δ=parameter to determine object boundary; and

D distance between x-ray source and iso-center.

5. A method in accordance with claim 2 wherein the average attenuation coefficient is:

$$\mu = \frac{\int_{-\gamma_m}^{\gamma_m} p(\gamma) d\gamma}{2\int_0^{\alpha_m} \sqrt{R^2 - ([D\sin(\gamma)])^2}\, d\gamma}$$

where p(γ) is the measured projection at detector angle γ.

6. A method in accordance with claim 2 wherein the attenuation index is:

$$\xi = R^{-1} \int_{-\gamma_m}^{\gamma_m} p(\gamma) d\gamma.$$

.

7. A method in accordance with claim 2 wherein processing the scout scan data further comprises the steps of:

determining a final membership grade; and measuring the variation of attenuation characteristics perpendicular to the scan plane.

8. A method in accordance with claim 7 further comprising the step of determining a collimator aperture index.

9. A method in accordance with claim 8 wherein the collimator aperture index is:

$$A_{index} = \frac{\theta}{\int_{-\gamma_m}^{\gamma_m} \Delta(\gamma) w(\gamma) d\gamma}$$

where θ is a parameter determined by the computed tomography system.

10. A method in accordance with claim 9 wherein the computed tomography system includes an image reconstructor, and wherein the collimator index is determined in the image reconstructor.

11. A method for identifying partial volume artifact producing objects in scan data, the scan data collected in a computed tomography system, said method comprising the steps of:

performing a scout scan of a patient; and processing the obtained scout scan data to determine the variation of attenuation characteristics perpendicular to the scan plane.

12. A method in accordance with claim 11 wherein the computed tomography includes an adjustable slice thickness collimator, said method further comprising the step of:

adjusting the collimator slice thickness based on the attenuation characteristics.

13. A method in accordance with claim 11 wherein processing the obtained scout scan data comprises the steps of:

identifying the boundaries of the objects;

estimating the radius of the objects;

determining an average attenuation coefficient; and determining an attenuation index.

14. A method in accordance with claim 11 wherein the image reconstruction comprises the step of:

adjusting the partial volume artifact correction based on the attenuation characteristics.

15. A system for reducing partial volume artifacts in scan data of a patient, the scan data collected in a tomographic scan, said system having an adjustable slice thickness collimator, said system configured to:

perform a scout scan of the patient;

process the obtained scout scan data to identify the presence of a partial volume artifact object; and adjust said collimator slice thickness based on the presence of the partial volume artifact object.

16. A system in accordance with claim 15 wherein to process the scout scan data, said system is configured to:

identify the boundaries of the object;

estimate the radius of the object;

determine an average attenuation coefficient; and determine an attenuation index.

17. A system in accordance with claim 16 wherein said radius of the object R is:

$$R = \frac{D\sin(\alpha)}{\sqrt{1-\delta^2}}$$

where:

α=angle formed by the boundary rays and the iso-ray;

δ=parameter to determine object boundary; and

D=distance between x-ray source and iso-center.

18. A system in accordance with claim 16 wherein the average attenuation coefficient is:

$$\mu = \frac{\int_{-\gamma_m}^{\gamma_m} p(\gamma)d\gamma}{2\int_0^{\alpha_m} \sqrt{R^2 - ([D\sin(\gamma)])^2}\, d\gamma}$$

where p(γ) is the measured projection at detector angle γ.

19. A system in accordance with claim 16 wherein the attenuation index is:

$$\xi = R^{-1}\int_{-\gamma_m}^{\gamma_m} p(\gamma)d\gamma.$$

.

20. A system in accordance with claim 16 wherein to process the scout scan data, said system is further configured to:

determine a final membership grade; and measure the variation of attenuation characteristics along the z axis.

21. A system in accordance with claim 20 wherein said system is further configured to determine a collimator aperture index.

22. A system in accordance with claim 20 wherein said collimator aperture index is:

$$A_{index} = \frac{\theta}{\int_{-\gamma_m}^{\gamma_m} \Delta(\gamma)w(\gamma)d\gamma}$$

where θ is a parameter determined by the computed tomography system.

* * * * *